US006764463B1

(12) United States Patent
Farris

(10) Patent No.: US 6,764,463 B1
(45) Date of Patent: Jul. 20, 2004

(54) METHOD AND NEEDLELESS APPARATUS FOR THE STORAGE OF A FIRST SUBSTANCE FOLLOWED BY SUBSEQUENT MIXING WITH A SECOND SUBSTANCE AND TRANSFER WITHOUT AMBIENT AIR INCURSION

(76) Inventor: Barry Farris, P.O. Box 1817, Zephyr Cove, NV (US) 89448

( * ) Notice: Subject to any disclaimer, the term of this patent is extended or adjusted under 35 U.S.C. 154(b) by 0 days.

(21) Appl. No.: 09/605,140

(22) Filed: Jun. 27, 2000

(51) Int. Cl.[7] ............................................. A61M 37/00
(52) U.S. Cl. ....................................................... 604/82
(58) Field of Search .............................. 604/82–89, 92, 604/93.01, 181, 187, 200, 212, 215–216, 217, 241–244, 256, 523, 533–535, 537, 538, 294–295; 128/919; 206/571, 363–366, 438; 137/3; 215/40, 47–48, 250, 253–254, 900

(56) References Cited

U.S. PATENT DOCUMENTS 4,643,309 A * 2/1987 Evers ......................... 206/364
4,722,733 A * 2/1988 Howson ...................... 604/411
4,915,689 A * 4/1990 Theeuwes ...................... 137/3
5,035,689 A * 7/1991 Schroeder ...................... 141/2
5,102,398 A 4/1992 Farris
5,261,881 A * 11/1993 Riner ......................... 128/919
5,370,626 A 12/1994 Farris
5,409,125 A * 4/1995 Kimber et al. ................ 215/48
5,538,506 A 7/1996 Farris et al.
5,716,346 A * 2/1998 Farris .......................... 215/249
5,897,008 A * 4/1999 Hansen ....................... 215/383
6,045,538 A 4/2000 Farris

* cited by examiner

*Primary Examiner*—LoAn H. Thanh
(74) *Attorney, Agent, or Firm*—Bernhard Kreten

(57) ABSTRACT

A method and an apparatus for the storage and transfer of a lyophilisate, oncolytic, mutagenic, or other prescription is disclosed. An ampule prior to its being sealed has an orifice at one end for the addition of the lyophilisate, for example or one component of a multi-component mixture. After placement of the lyophilisate, the orifice is sealed. The ampule has a body portion formed with flexibly deformable walls and with the sealed orifice defines a blind bore. An opening of the ampule is also included and has a tapered section adapted to frictionally fit over a taper of a male luer-type fitting commonly found on syringes and needleless cannulas. The opening is protected by a frangible cap integrally formed during manufacture. By removing the cap and docking the opening with a syringe, liquid enters the ampule for mixing with the dry contents in the ampule without ambient air.

27 Claims, 7 Drawing Sheets

METHOD AND NEEDLELESS APPARATUS FOR THE STORAGE OF A FIRST SUBSTANCE FOLLOWED BY SUBSEQUENT MIXING WITH A SECOND SUBSTANCE AND TRANSFER WITHOUT AMBIENT AIR INCURSION

FIELD OF THE INVENTION

The following invention relates generally to a method and apparatus for storing a first substance, preferably dry, activating the first substance with a second substance, preferably a liquid, and subsequently transferring the diluted, mixed substance from storage into a syringe or cannula without the need for a needle and without appreciable contact with ambient air. More particularly, the present invention relates to a storage container for storing a substance that has undergone a lyophilization process and is ready for the introduction of a substance to evolve into a medium that may be then utilized according to its appropriate prescription. More specifically, the instant invention is specifically tailored to inhibit the lability of pharmaceuticals or extend its useful shelf life.

BACKGROUND OF THE INVENTION

The potency, efficacy, freshness and/or safety of many substances degrade over time. For example, powder mixed with a diluent has a shelf life of 72 hours or less, while lyophilized powder alone has a shelf life of years. FDA regulations require manufacturers to mark their ready to use and unmixed products identifying a date of expiration which states explicitly that the contents contained therein will not be as effective, fresh or safe to use subsequent to the date printed on the identification mark. This is of particular concern to pharmaceutical companies dealing with the efficacy of their pharmaceutical products degrading over time, because of many pharmaceuticals' labile nature. This degradation may reach a point where using the particular pharmaceutical product beyond the date imprinted on the bottle could result in the pharmaceutical providing no effect, not enough effect or negative effects on persons taking the product as prescribed by the pharmaceutical manufacturer's directions, distributor's directions, seller's directions, product's directions, pharmacy's directions and/or the attending physician's directions. With lyophilized products, directions for use after mixing typically mandate use before a certain number of hours. The onus for proper use at this point shifts from the manufacturer to the caregiver.

The instant invention chronicles the ongoing efforts of the applicant to address the needs of the medical community. Applicant's issued patents are as follows: U.S. Pat. Nos. 5,102,398; 5,370,626; 5,538,506; 5,716,346; and 6,045,538.

SUMMARY OF THE INVENTION

The instant invention inhibits the labile nature of substances. In its most elemental form, the instant invention is a specialized container to store dry product. In particular, the instant invention takes advantage of the lyophilic process and provides a container for storing the lyophilisate to inhibit the lability of pharmaceutical products. In this patent application, the container is to be called an ampule. This container provides an aseptic environment that prevents bacteria from propagating to the pharmaceutical product which would effect the product in an adverse manner. The container is configured to receive liquid in such a way that the dry product can be diluted without appreciable exposure to ambient air. Because powder alone and powder mixed with a substance can be mutagenic, confined mixing without dispersion, released/aero solution or contamination is critical, and the instant invention addresses these critical concerns.

Further, the instant invention provides for a process that dissolves a dry, powdery or dry, pelletized substance stored in a dry, plastic ampule. The ampule has a first coupler defining an outlet which has been sealed during manufacture by occluding the first coupler outlet with a first cap.

To use the dry substance, it must first be dissolved. The cap is removed, exposing the coupler/outlet and liquid is introduced. The powder is dissolved and the resulting mixture is removed for use.

The container is constructed to discourage any appreciable ambient air from contaminating the system. This minimizes nosocomial infections.

Further, the instant invention completely avoids the use of a needle. The instant invention takes advantage of a coupling that is the standard on a majority of syringes which had heretofore only been used in the past to support the hypodermic needle on the syringe. This coupling, called a luer fitting, has a male component and a female component. Typically, the syringe is configured with the "male" luer coupling which appears as a truncated cone that has an opening at its end. Some luer couplings are threaded. The luer coupling typically diverges toward an interior cylindrical hollow portion of the syringe. The coupler of the instant invention replicates the "female" luer coupling normally associated with the needle per se. Preferably liquid is introduced via a syringe by connecting the respective luer couplers of the syringe and ampule. The coupler provides a tight, reliable seal. The walls of the ampule are flexible. Flexible walls not only promote removal of liquid, but also avoid introducing ambient air into the ampule. Instead of venting air at the coupler, the walls of the ampule flex.

The syringe can be prefilled in as described in U.S. Pat. No. 5,102,398 or can be filled as described in U.S. Pat. No. 5,716,346.

Once filled, the syringe feeds the ampule with liquid for mixing. After mixing, the contents of the ampule is then retransferred back to the syringe (while preferably still docked to the ampule) with none or a minimal, negligible amount of ambient air introduced. The flexible side walls of the ampule can collapse as the liquid from the ampule is loaded into the syringe but it is primarily the coupling that eliminates ambient air invasion.

Once the ampule has been removed, a syringe has the intended mixture of medication disposed therewithin. Unlike the prior art, no needle has yet been involved. Also, no air from the ambient environment has been mixed with the sterile fluid as was the case with rigid wall containers that require pressurization.

In one form of the invention, it is contemplated that the opening associated with the ampule is provided with a removable cap having a luer-type coupling and an indicia bearing tab. The medicinal contents of the ampule is stamped on the tab for identification purposes. With such an arrangement, it is possible to transfer the cap and tab from the ampule and connect the cap to the syringe to provide a tell tale of the contents of the fluid contained within the syringe. As an alternative, the ampule could remain docked to the syringe until actual use to act both as a sterility cap and identify the substance in the syringe because the ampule would also note the contents on a surface thereof.

As a result of this system, the entire process for dissolving and mixing a dry substance and then filling a syringe has been accomplished without the use of a needle. Personnel are able to operate more quickly with less fear of either inadvertent needle stick or inadvertent exposure to the medicine contained within the syringe.

It is to be noted that for many in-patients, the standard procedure in a hospital is to tap into a person's vein only once with an infusion catheter and to leave the catheter needle in place with tubing communicating therewith so that subsequent fluids such as intravenous drips and the like can be used. With such a system, a needle would never be needed with the syringe according to the present invention. "Y" connectors are well known in the art, one branch of which and would have a complemental female luer coupling. Thus, for a patient's entire stay at a hospital, the only needle associated with that one patient, ideally, would be the one which initially had been placed in the patient's vein to support the infusion catheter. In this way, the opportunity for inadvertent needle sticks would be reduced to a minimum.

OBJECTS OF THE INVENTION

Accordingly, the primary object of the present invention is to provide a method and apparatus for transferring sterile fluid from an ampule to a hypodermic syringe after mixing liquid and solids in the ampule without the need of a hypodermic needle and without ambient air contamination.

It is a further object of the present invention to provide a device and method as characterized above which reduces the amount of time which hospital staff must spend in transferring fluid from a sterile ampule to a hypodermic syringe while also eliminating the fear of an inadvertent needle stick, thereby avoiding the possibility of both unwanted contamination and unwanted medication being released into and/or exposed to the air.

A further object of the present invention contemplates providing a device and method as characterized above which is extremely inexpensive to fabricate, safe to use and lends itself to mass production techniques.

A further object of the present invention is to provide a device which can reduce the number of times that needles are required in a hospital or other medical setting.

A further object of the present invention contemplates providing a device and method which minimizes the disposal problems of hypodermic syringes with needles.

A further object of the present invention contemplates providing a device and method for use in which a telltale is associated with first the ampule that stores the medicine, and then the syringe so that the fluid transferred from the ampule and into the syringe will be known at all times. In this way, the chain of custody of the fluid can be more readily monitored.

A further object of the present invention contemplates providing a system for loading syringes that obviates the need for the medicating health professional from having to trundle a miniature pharmacy on a cart from patient to patient. By filling the syringes at the patient's bed side, added security, safety and efficiency may be provided.

Viewed from a first vantage point it is an object of the present invention to provide a needleless system for mixing a sterile liquid with a dry substance. A syringe docks with an ampule having a substance such as a lyophilized material for mixing and subsequent timely use. The ampule is defined by an end, collapsible side walls extending from the end thereby defining a blind bore and having an open end, a coupler at the open end, and a removable cap occluding the open end at the coupler. The coupler is provided with means to connect to a needleless opening of the syringe to be in fluid communication therewith, whereby fluid can be transferred without an interconnecting needle. When the syringe docks with the ampule, after the liquid and solids are mixed the syringe is loaded with the mixture.

Viewed from a second vantage point, it is an object of the present invention to provide a method for forming an ampule to transfer medicine to be infused in a patient. The steps include forming an ampule with resilient walls so that the ampule can be collapsed, and forming an opening on the ampule. The opening is circumscribed by a coupler which is fashioned to receive a dose administering device. The ampule houses dry medicine. The ampule opening is sealed until use.

Viewed from a third vantage point, it is an object of the present invention to provide for a process that dissolves a dry or powdery or pelletized substance stored in an ampule. The ampule has a coupler defining the outlet and which has been sealed by occluding the coupler outlet with a cap. A needleless syringe is configured with a coupler and an opening which communicates within an interior cylindrical hollow of the syringe so that fluid passes by the coupler through the opening and into the cylindrical hollow and fills the syringe. The steps include removing the cap from the ampule and orient the coupler of the ampule with the coupler of the syringe into complemental, fluid-tight locking engagement so that the opening of the ampule registers with the opening of the syringe. Next, transfer the fluid of the syringe into the ampule; mix the dry substance in the ampule with the fluid from the syringe until the dry substance is dissolved thus making a mixture preferably while the ampule and syringe remain mated. Then convey the mixture back into the syringe for inserting the mixture into a patient. The mixture may be filtered prior to dispensation.

Viewed from a fourth vantage point, it is an object of the present invention to provide for another process for forming an ampule to transfer pharmaceutical grade fluid or solid to be administered. The process includes: forming an ampule with resilient walls so that the ampule can be collapsed and creating an orifice to pass the pharmaceutical grade fluid or solid into the ampule and then sealing the orifice; also forming an opening on the ampule and sealing with a cap. A scoreline at the juncture with the cap is such that the opening defines a coupler which is to be complementally fastened to and receives a dose administering device.

Viewed from a fifth vantage point, it is an object of the present invention to provide for an ampule for storing a pharmaceutical product in a manner to inhibit lability of the product and permitting the transfer of the product in an aseptic manner to avoid nosocomial infection from ambient air. The ampule has resilient walls that can be collapsed and includes an orifice to pass a pharmaceutical grade fluid or solid therethrough and an opening on said ampule whereby the opening defines a coupler which is to be complementally fastened to receive a dose administering device.

These and other objects were made manifest when considering the following detailed specification when taken into conjunction with the appended drawing figures.

DESCRIPTION OF PREFERRED EMBODIMENTS

Figure 1:
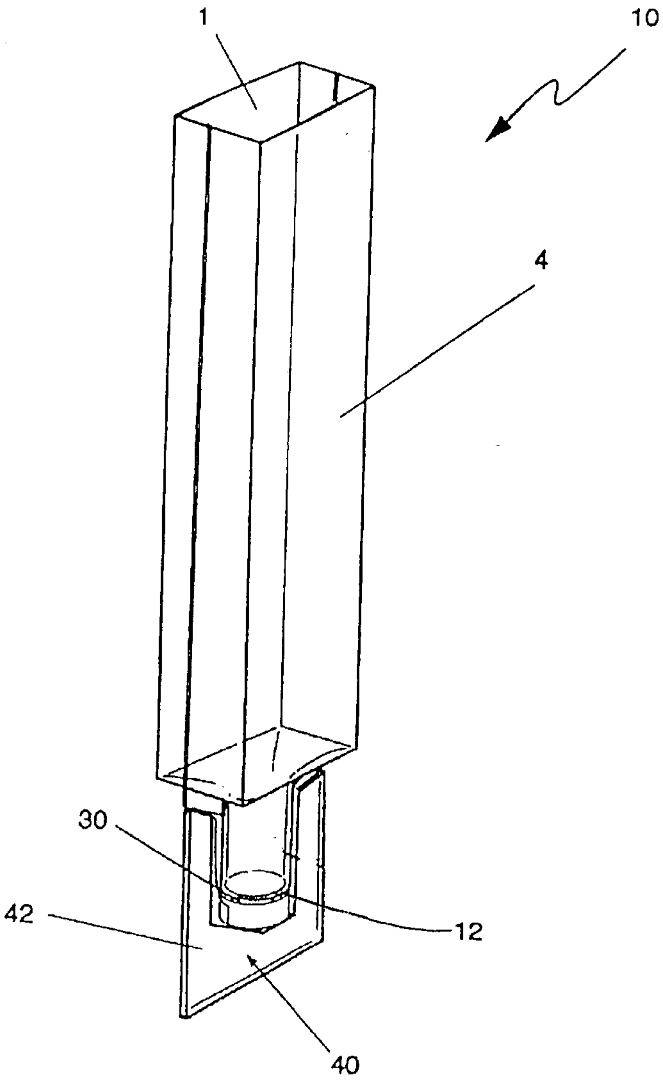
FIG. 1 is a perspective view of the ampule according to the present invention showing an open orifice which is ready to accept medication.
Figure 1A:
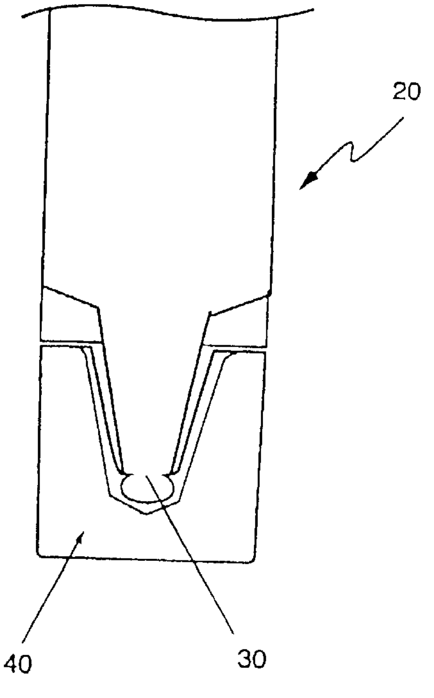
FIG. 1A details a feature of FIG. 1.

Considering the drawings, wherein like reference numerals denote like parts throughout the various drawing figures, reference numeral 10 is directed to the ampule according to the present invention.

While the term "ampule" and "vial" have common, somewhat interchangeable meaning in the art, for clarity the term "vial" as used herein reflects structure described in detail in U.S. Pat. Nos. 5,716,346 and 6,045,538, while ampule refers to reference number 10. These word choices should not be construed as limitations.

Figure 3:
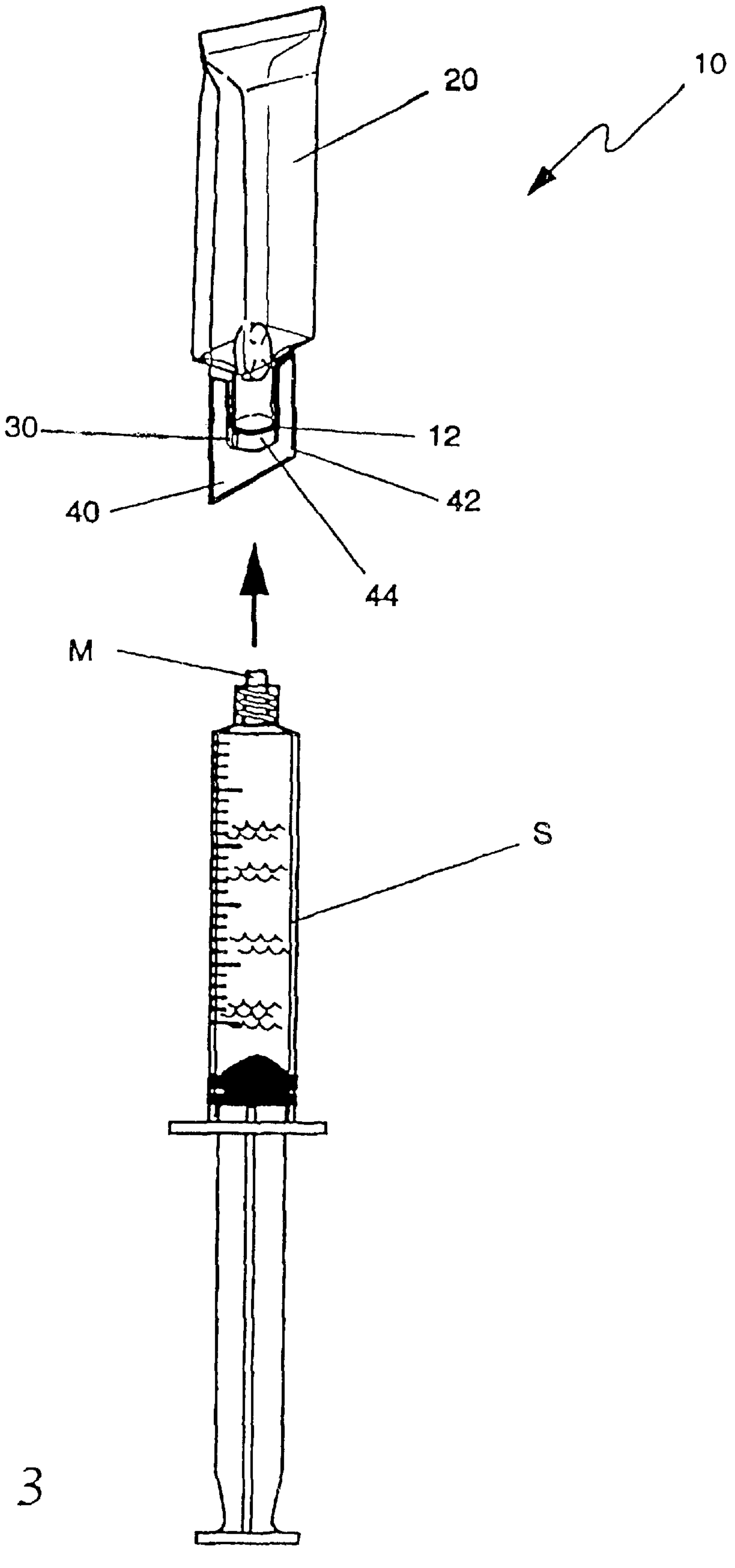
FIG. 3 shows an ampule's contents about to be mixed with a syringe's liquid.
Figure 4:
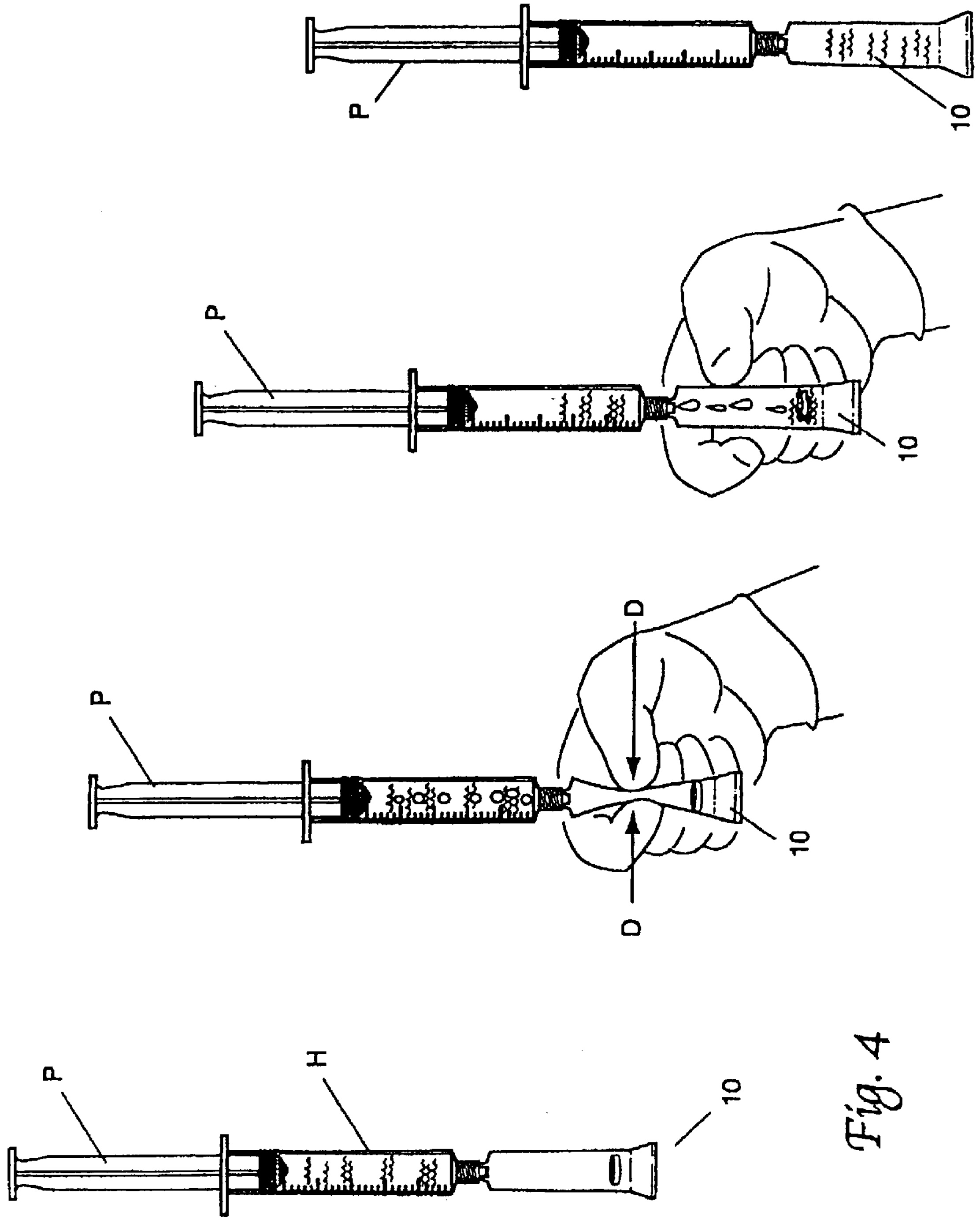
FIG. 4 shows a series of views of the syringe of FIG. 3 engaged with the ampule depicting the preferred steps of manipulating the liquid into the ampule to dissolve the ampule's powder or tablet.

In its essence, and viewing FIG. 3, the ampule 10 is formed from two parts: a body portion 20 and a cap portion 40. An area of transition noted as a scoreline 30 serves as an area of demarcation between the cap 40 and body 20. The scoreline 30 allows the cap 40 to be dissociated from the body 20 so that the body 20 can dock with a syringe S as shown in FIG. 4 for filling the body 20 with the solution necessary to dissolve the powder 100 (or tablet 110) within the ampule 10 and subsequently to refill the syringe S (FIG. 6) with fluid F containing the now dissolved powder 100 ready for injection. An opening 12 (FIG. 5A) at the scoreline 30 tightly fits over the syringe's luer M.

Figure 2A:
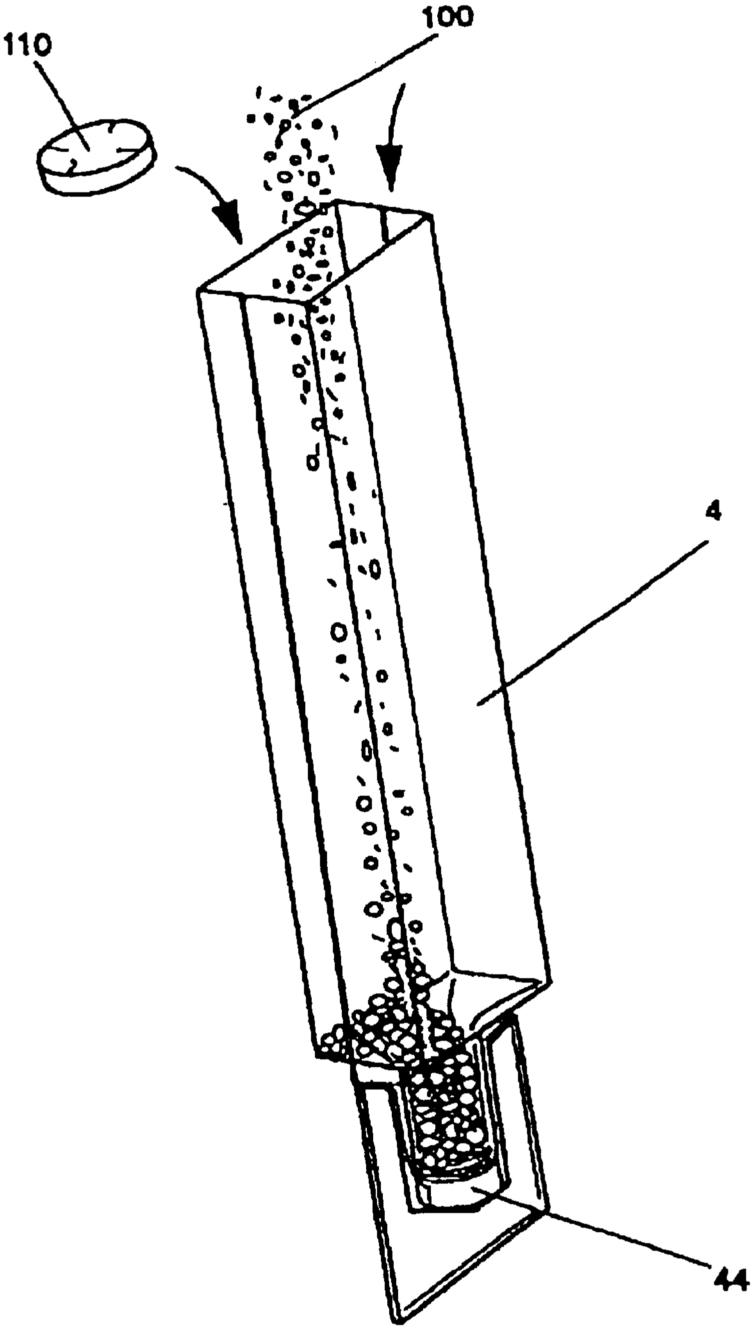
FIG. 2A is a perspective view of the ampule of FIG. 1 having free flow powder or a compressed tablet of medication inserted therein.
Figure 2B:
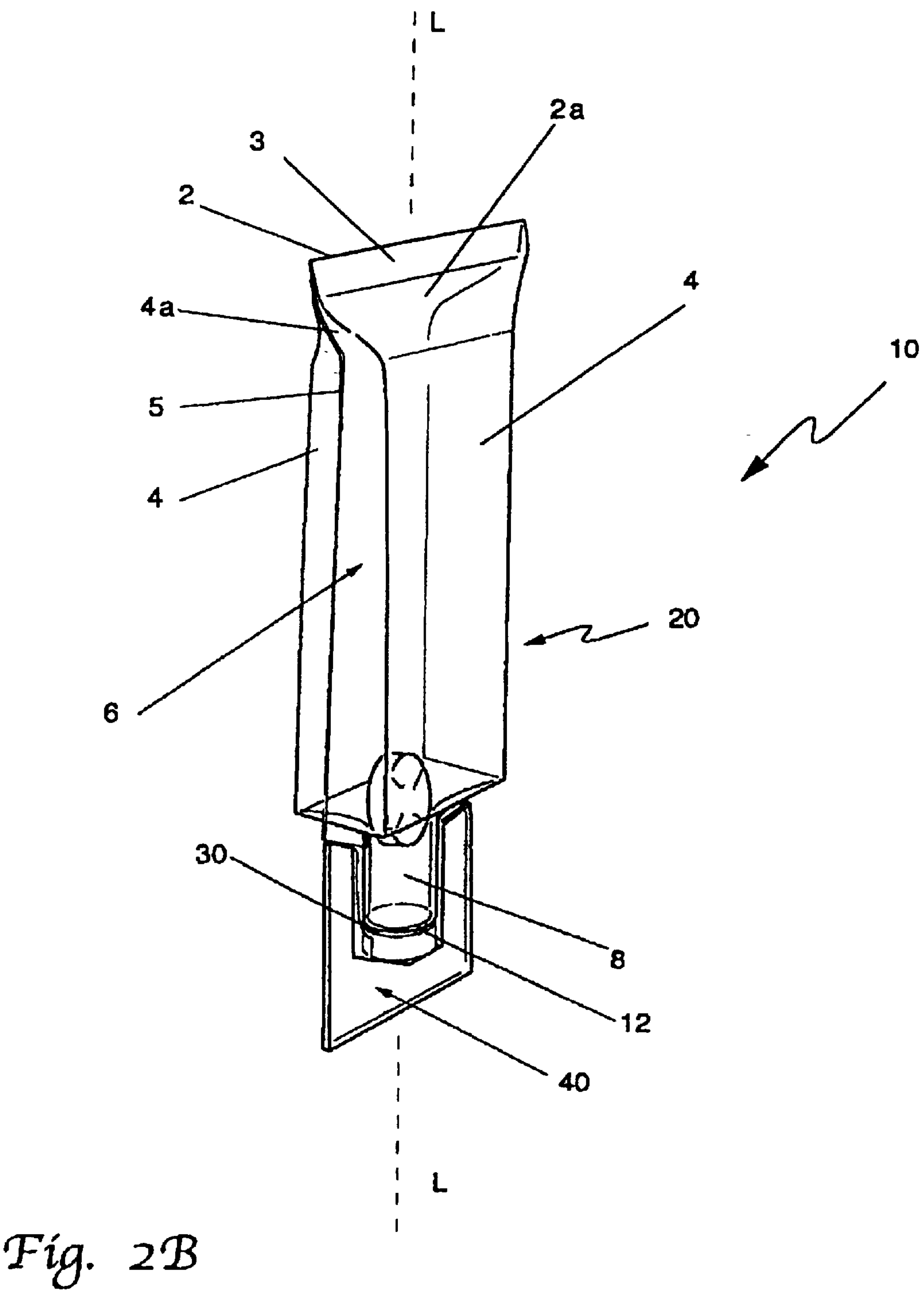
FIG. 2B shows the ampule of FIG. 2A with the orifice closed and sealed.

More specifically, and referring to the drawings in detail, the ampule 10 includes a body 20 having an orifice 1 (FIG. 1) for permitting the placement of free flow powder 100 or alternatively a compressed tablet 110 (FIG. 2A). After insertion of powder 100 or tablet 110 into ampule 10, the orifice 1 is hermetically and aseptically sealed forming an end wall 2 that includes a fan-shaped seam 3 (FIG. 2B). The seam 3 is preferably formed by heat sealing free ends of side walls 4. Preferably the gas contained in the ampule 10 is pure, sterile and inert as to the ampule's contents during controlled filling and sealing. Prior to sealing, peripheral side walls 4 initially have one proximal free end coterminous with an outer periphery of the end wall 2. Side walls 4 extend away from the end wall 2 so that a blind bore 6 has been formed within which the powder 100 or tablet 110 is to be stored. As shown, the side walls 4 can be a substantially rectangular prism in shape, see FIG. 2B. The fan seam 3 and end wall 2 is formed by fusing together opposite faces of two side walls 4. The remaining two sides are provided with fold lines 5 to facilitate closure of the orifice 1 so that end wall 2 includes angled roof like facets 2A leading to seam 3 which projects up from an apex of the roof. Fold lines 5 define truncated eaves 4*a* adjacent seam 3 and facet 2A.

Typically, dry powders and tablets such as a pharmaceutical drug or other medicaments can be stored within the blind bore 6. The list of possible medicaments is large and includes as examples: common injectables, oncolytics, mutagenics, toxins and environmentally dangerous drugs (e.g. 5FU).

A distal end of the side wall 4 remote from the end wall 2 is provided with a slight tapering section 8 (FIG. 5A) which converges towards a longitudinal axis L (FIG. 2A) of the ampule 10 defining a converging end of the ampule 10. This tapering section 8 converges to an opening 12 (FIG. 5A), or outlet and thereafter communicates with the cap 40. The opening 12 defines a coupler of the ampule 10. The area where the opening 12 is located is preferably coincident with the scoreline 30 to facilitate fracture of the ampule 10 precisely at the opening 12. Thus, the cap 40 can be separated from the body 20.

The cap 40 includes a flag type tab 42 (FIG. 5B) on an exterior surface thereof upon which is printed the product contained within the ampule 10. The tab 42 is shown having a substantially rectangular, planar configuration to provide an exposed surface sufficient to place the name of the product on the tab. The tab 42 also serves as a purchase area to allow a person to grasp the cap 40 so that a twisting motion of the cap 40 with respect to the body 20 will cause severing of the body 20 from the cap 40 at the scoreline 30. The body 20 preferably also bears the name of the product on an exterior surface.

The cap 40 also includes an interior passageway 44 having a diverging contour (FIG. 5B) which substantially mirrors the slope of the tapered section 8 of the body 20 of the ampule 10 about an axis of symmetry coincident with the scoreline 30. This diverging passageway 44 extends a short distance within the cap 40 for purposes to be assigned. Taper 8, scoreline 30 (at opening 12) and passage way 44 define a converging—diverging throat with the throat located at scoreline 30.

As shown in FIG. 3, prior to docking with the syringe S (or needleless cannula), the cap 40 will have to be removed from the body 20 of the ampule 10. This allows the opening 12 of the body 20 to be exposed. The opening 12 has an inner peripheral dimension complemental to an exterior diameter of a male luer coupling M or spike found on the syringe's or cannula's outlet. See FIG. 5A. This coupling M defines an opening whose outer surface forms a coupler of the syringe. Typically, this luer-type connection M tapers and diverges as it approaches a cylindrical hollow housing H of the syringe S. Thus the coupling M narrows as it extends away from the hollow H. (See FIG. 5A.) The luer may also include a peripherally circumscribing collar with an internal thread T.

Figure 5A:
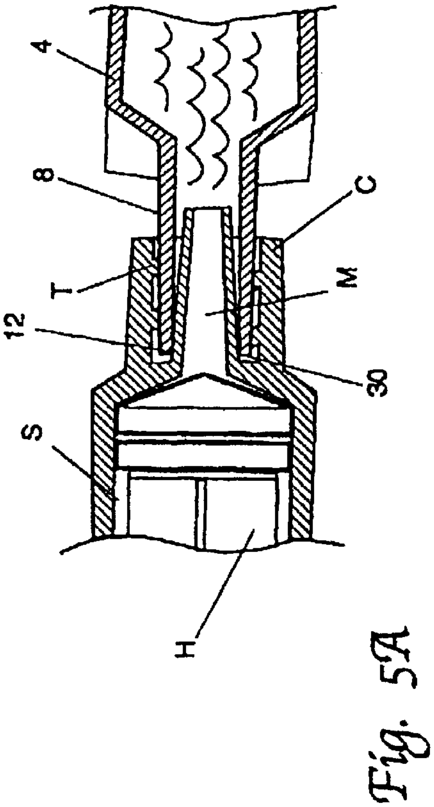
FIG. 5A details the converging opening of the ampule body.

For a friction fit, and with respect to the syringe S, the taper of the luer M traditionally couples to a needle. Instead, the syringe docks with the ampule 10 as shown in FIG. 5A such that the "male" conical taper of luer coupling M of the syringe S passes within the female opening 12 of the body 20 and becomes frictionally engaged at the opening 12, extending into the tapering section 8 of the ampule's body 20. This coupling is very tight because of the wedging effect of luer M within taper 8 at opening 12. The effect can be enhanced by taper 8 threading into threads T on collar C. The connection is substantially air tight.

FIG. 4 picture series shows loading the ampule from a full syringe. Rather than push the syringe's contents into the ampule, it is preferred to "milk" the liquid out of the syringe, relying on the very tight seal between the syringe and the ampule (FIG. 5A). Squeezing the ampule along arrows D causes the syringe plunger P to remain out of its housing H with an ultimately dry syringe (right hand side if FIG. 5). Milking the ampule 10 involves gentle squeezing. This technique allows transfer to the ampule without ambient air entering.

Figure 6:
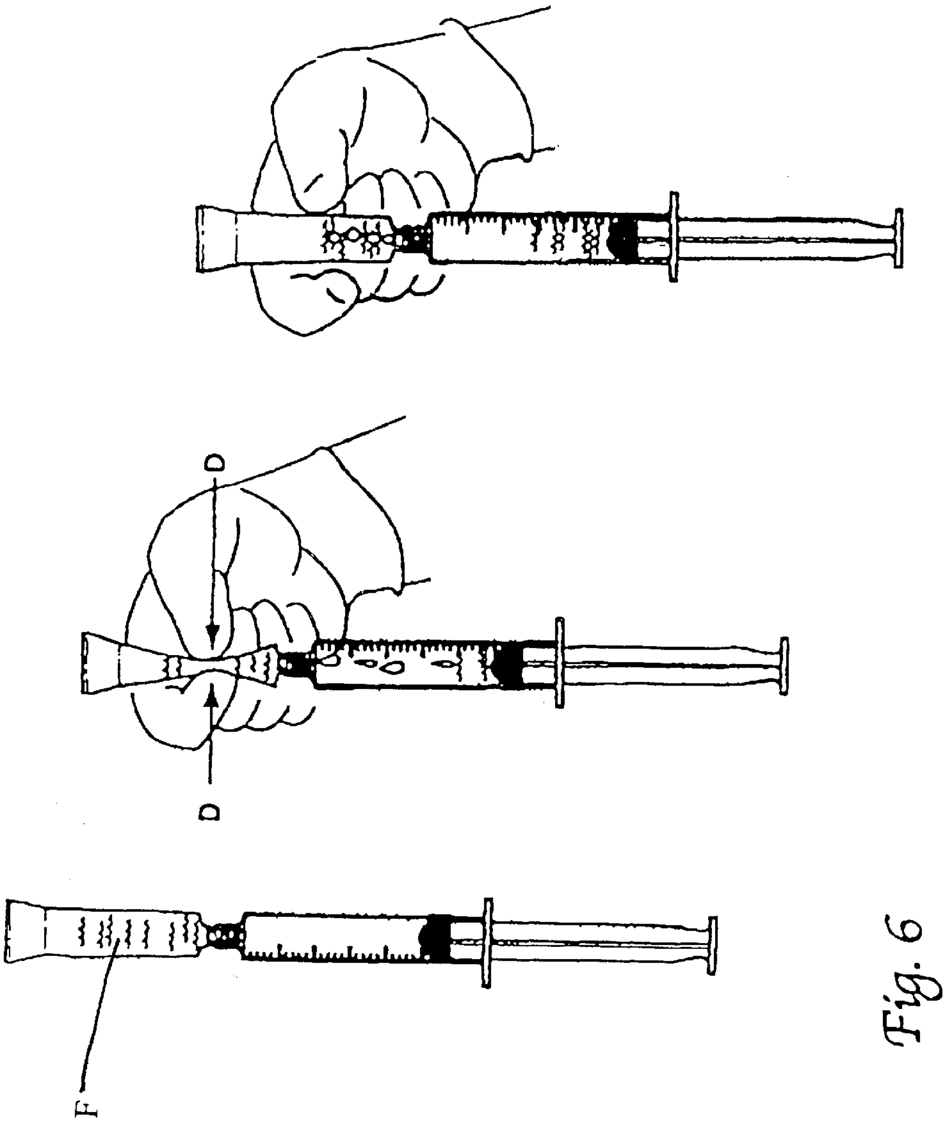
FIG. 6 shows a series of views just after mixing the solution made from the liquid and the now dissolved powder or tablet and the preferred technique of reintroducing the solution back to the syringe. The right side view shows the ampule after having been separated from the now loaded syringe after fluid extraction from the ampule.

With respect to FIG. 6, it should be recalled that the side walls 4 of the ampule 10 are formed from a material having the ability to elastically deform in the presence of force. In other words, the side walls 4 of the body of the ampule 10 can collapse. In this way, fluid F contained within the ampule 10 can be transferred from and back into the syringe S after mixing with the dry contents of the ampule without admitting ambient air into its ampule 10 or syringe.

The ampule 10 is deformed by providing external force in the direction of the arrows D along the outer periphery of the side walls 4. This causes the incompressible fluid F to be forced from the ampule 10 and back into the syringe S. The plunger P will remain in the filled position. The cylindrical hollow H of the syringe S receives the fluid F. In other words, the syringe S will now have been filled with the fluid F and the plunger P will remain extended in position for delivery to a patient without introduction of any ambient air.

Figure 5B:
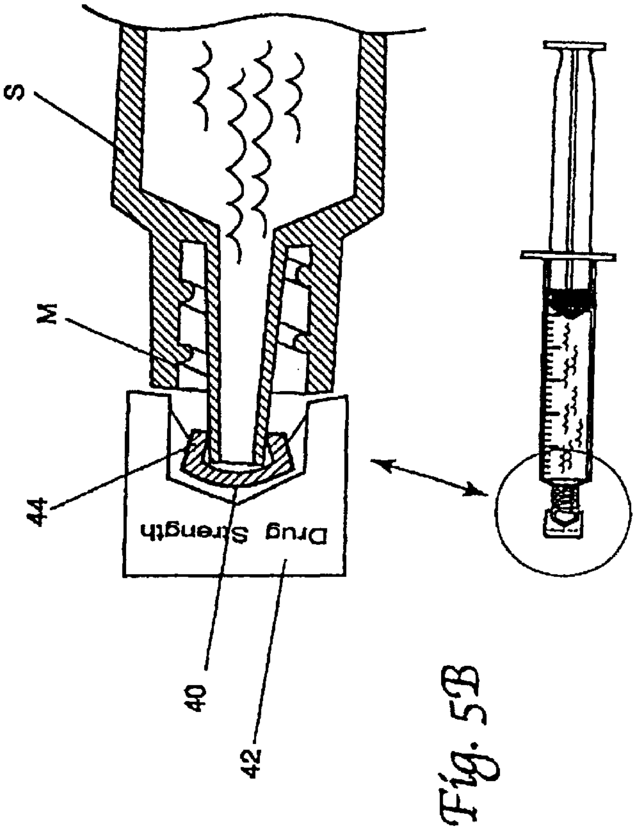
FIG. 5B details the diverging opening of the ampule cap.

In this way, after the syringe S is loaded and ready for subsequent use, the contents of the fluid F within the syringe S will be ready for dispensing the medication to the patient. Different fluids can be pre-loaded into several syringes in a secure area. The healthcare professional can merely take a collection of the syringes or needleless cannulas to the site for ultimate medicating without having to use a drug preparation cart as is commonly in vogue today. Since the cap 40 (as shown in FIG. 5B) and body 20 (as shown in FIG. 5A) both are to fit the syringe or cannula, the syringe or cannula's contents can be verified at use.

As had been mentioned briefly hereinabove, most hospital in-patients have infusion catheters operatively coupled at all times during their stay. Many of the infusion catheters include a female luer coupling compatible to the contour of syringe S. When this is the case, the syringe S never needs to include a needle on the male luer coupling M. Instead, one can administer the medicine directly into the infusion catheter via catheter inlet. In this way, the number of instances where trained medical personnel are exposed to administering fluids with hypodermic needles will be minimal. This reduces the amount of time and care required in the efficient performance of their tasks and minimizes both occasions for needle sticks and problems of needle disposal.

In use and operation, a filled syringe S docks with the ampule 10 of FIG. 4, which was opened by removing cap 40. The contents of the syringe enter the ampule. Preferably the ampule's volume is greater than the sum of the volume introduced by the syringe and the initial contents of the ampule, preferably greater than or equal to 125%. This allows good agitation and mixing. The contents are mixed (preferably with the syringe still attached), dissolving the dry matter of the ampule with the liquid from the syringe. The syringe, still docked to the ampule is then loaded with the liquid mixture. Optionally, a filter may be initially interposed between the ampule 10 and syringe S or subsequently between the syringe and a conventional needle or catheter inlet. When drawing the liquid through the filter, undissolved matter is entrained in the filter. The syringe is then ready for use.

While the contents of the ampule 10 has been described as preferably a powder or tablet, it more generally be thought of as one component in a two component system when mixed with the contents (the second component) of the syringe. Typically the syringe's contents is a diluent liquid such as saline or sterile water, but it could be a catalyst, reagent or component which when mixed initiates a chemical reaction. Further a powder or tablet is to mean any dry substance. When mixed with the syringe's contents, the result can be a diluted product, a new solution, a suspension, etc. While the ampule's fluid is preferably sterile air, it may be another fluid, perhaps an inert gas. Two key factors are the needleless aspect and the preclusion of ambient air.

Thus, a method and an apparatus for the storage and transfer of a lyophilisate, oncolytic, mutagenic, or other prescription is disclosed. An ampule prior to its being sealed has an orifice at one end for the addition of the lyophilisate, for example or one component of a multi-component mixture. After placement of the lyophilisate, the orifice is sealed. The ampule has a body portion formed with flexibly deformable walls and with the sealed orifice defines a blind bore. An opening of the ampule is also included and has a tapered section adapted to frictionally fit over a taper of a male luer-type fitting commonly found on syringes and needleless cannulas. The opening is protected by a frangible cap integrally formed during manufacture. By removing the cap and docking the opening with a syringe, liquid enters the ampule for mixing with the dry contents in the ampule without ambient air. After mixing, the solution is then removed from the ampule. Fluid is forced from the ampule opening into a syringe without ambient air. The opening of the ampule is initially protected with the cap that includes a scoreline which, when fractured, defines the opening. The cap to be removed from the ampule prior to its use is fabricated as one piece with the ampule preferably using a blow, fill, seal or injection molding technique in order to assure sterile conditions during manufacture and filling. A tab is associated with the cap which lists the ingredients within the ampule. The ampule also exhibits an area which lists the ampule's contents. The cap is specifically structured with a coupling so that after its removal from the ampule, it can frictionally engage the luer opening of the syringe or a cannula. The tab provides indicia thereon as to the contents within the thus loaded syringe and to temporarily seal the syringe or cannula. The disclosed needleless dosage transfer system for filling medicating devices such as syringes or needleless cannulas minimizes the likelihood of an unwanted needle stick and to avoid the initial cost of a needle as well as the disposal cost of the needle. departing from the scope and fair meaning of the instant invention as set forth hereinabove and as defined hereinbelow by the claims.

I claim:

1. A needleless dosage transfer system, comprising in combination:

an ampule defined by an end wall and side walls extending from said end wall thereby defining a blind bore and an open end, said side walls formed from resilient, collapsible material, a dry substance in said ampule, a coupler defined by said open end of said ampule, and a removable cap occluding said open end, said cap integrally formed at said open end and removed at a score line;

said coupler having means to connect to a syringe or cannula in operative communication therewith, such that liquid can be directly transferred to and from said ampule without an interconnecting needle.

2. The system of claim 1 wherein said coupler at said open end of said ampule includes a converging portion as it extends from said ampule side walls to said open end.

3. The system of claim 2 wherein said open end is initially integrally formed with said cap and is dissociated from said removable cap by means of a scoreline formed on said ampule at said opening.

4. The system of claim 1 wherein said cap includes indicia means on an exterior surface thereof correlative with the dry substance within said ampule.

5. The system of claim 1 wherein said dry substance is a powder.

6. The system of claim 1 wherein said dry substance is a solid tablet.

7. The system of claim 1 wherein said dry substance is selected from the group including common injectables, oncolytics, mutagenics, toxins, and environmentally dangerous drugs.

8. The system of claim 1 wherein said end wall is configured as a fan-shaped seam formed by heat sealed free ends of said side walls, forming fold lines along said side walls.

9. An ampule for storing a pharmaceutical product in a manner to inhibit lability of the product and permitting the transfer of the product in an aseptic manner to avoid nosocomial infection from ambient air comprising, in combination:

resilient walls that can be collapsed;

a sealable orifice adjacent said walls to pass a pharmaceutical grade solid therethrough;

and opening on said ampule a cap for occluding said opening; a scoreline proximate said opening whereby any content within said ampule can be accessed by severing said cap from said ampule at said scoreline, said opening is circumscribed by a coupler which is to be complementally fastened to receive a dose administering device.

10. The ampule of claim 9 wherein said cap is formed with an interior passageway having a dimension complemental to an outlet of a syringe or cannula for frictional engagement thereover after having been removed from said ampule.

11. The ampule of claim 9 wherein said cap has a tab surface.

12. The ampule of claim 11 wherein said tab surface includes indicia thereon correlative of contents within the ampule.

13. A needleless dosage transfer system, comprising in combination:

an ampule for storing a pharmaceutical product in a manner to inhibit lability of the product and permitting the transfer of the product in an aseptic manner to avoid nosocomial infection from ambient air comprising, in combination:

resilient walls that can be collapsed;

a sealable orifice adjacent said walls to pass a pharmaceutical grade solid therethrough;

and an opening on said ampule, said opening is circumscribed by a coupler which is to be complementally fastened to receive a dose administering device, said opening protected by a removable cap which is removed at a score line at said opening.

14. The system of claim 13 wherein said ampule further includes a cap for occluding said opening.

15. The system of claim 14 wherein said ampule further includes a scoreline proximate said opening whereby any contents within said ampule can be accessed by severing said cap for said ampule at said scoreline.

16. The system of claim 14 wherein said cap is formed with an interior passageway having a dimension complemental to an outlet of a syringe or cannula for frictional engagement thereover after having been removed from said ampule.

17. The system of claim 14 wherein said cap has a tab surface.

18. A needleless dosage transfer system, comprising in combination:

an ampule defined by an end wall and side walls extending from said end wall thereby defining a blind bore and an open end, said side walls formed from resilient, collapsible material, a dry substance in said ampule, and a coupler defined by said open end of said ampule, and a removable cap occluding said open end, said cap removed from said open end at a score line, said coupler having means to connect to a syringe or cannula in operative communication therewith, such that liquid can be directly transferred to and from said ampule without an interconnecting needle, wherein said dry substance is selected from the group including common injectables, oncolytics, mutagenics, toxins, and environmentally dangerous drugs, wherein said ampule includes sterile gas which is inert as to the dry substance contained therein.

19. A needleless dosage transfer system, comprising in combination:

an ampule defined by an end wall and side walls extending from said end wall thereby defining a blind bore and an open end, said side walls formed from resilient, collapsible material, a dry substance in said ampule, a coupler defined by said open end of said ampule, and a removable cap occluding said open end, said cap removed from said open end at a scoreline, said coupler having means to connect to a syringe or cannula in operative communication therewith, such that liquid can be directly transferred to and from said ampule without an interconnecting needle, and wherein said ampule includes sterile gas which is inert as to the dry substance contained therein.

20. A needleless dosage transfer system, comprising in combination:

an ampule defined by an end wall and side walls extending from said end wall thereby defining a blind bore and an open end, said side walls formed from resilient, collapsible material, a dry substance in said ampule, a coupler defined by said open end of said ampule, and a removable cap occluding said open end, said coupler having means to connect to a syringe or cannula in operative communication therewith, such that liquid can be directly transferred to and from said ampule without an interconnecting needle wherein said coupler at said open end of said ampule includes a converging portion as it extends from said ampule side walls to said open end wherein said open end is initially integrally formed with said cap and is dissociated from said removable cap by means of a scoreline formed on said ampule at said opening.

21. The system of claim 20 wherein said removable cap includes an interior passageway similar to said converging portion of said ampule adjacent said opening so that an axis of symmetry is provided at said scoreline.

22. The system of claim 21 wherein said passageway of said removable cap is dimensioned to frictionally override an opening of said needleless syringe or cannula which had been used to receive contents from the ampule whereby indicia on said removable cap travels with the needless syringe or cannula correlative of the contents within said syringe which heretofore had been in said ampule.

23. A needleless dosage transfer system, comprising in combination:

an ampule defined by an end wall and side walls extending from said end wall thereby defining a blind bore and an open end, said side walls formed from resilient, collapsible material, a dry substance in said ampule, a coupler defined by said open end of said ampule, and a removable cap occluding said open end, said coupler having means to connect to a syringe or cannula in operative communication therewith, such that liquid can be directly transferred to and from said ampule without an interconnecting needle wherein said cap includes indicia means on an exterior surface thereof correlative with the dry substance within said ampule.

24. A needleless dosage transfer system, comprising in combination:

an ampule defined by an end wall and side walls extending from said end wall thereby defining a blind bore and an open end, said side walls formed from resilient, collapsible material, a dry substance in said ampule, a coupler defined by said open end of said ampule, and a removable cap occluding said open end, said coupler having means to connect to a syringe or cannula in operative communication therewith, such that liquid can be directly transferred to and from said ampule without an interconnecting needle wherein said end wall is configured as a fan-shaped seam formed by heat sealed free ends of said side walls, forming fold lines along said side walls.

25. A needleless dosage transfer system, comprising in combination:

an ampule for storing a pharmaceutical product in a manner to inhibit lability of the product and permitting the transfer of the product in an aseptic manner to avoid nosocomial infection from ambient air comprising, in combination:

resilient walls that can be collapsed;

a sealable orifice adjacent said walls to pass a pharmaceutical grade solid therethrough;

and an opening on said ampule, said opening is circumscribed by a coupler which is to be complementally fastened to receive a dose administering device wherein said ampule further includes a cap for occluding said opening wherein said ampule further includes a scoreline proximate said opening whereby any contents within said ampule can be accessed by severing said cap for said ampule at said scoreline.

26. A needleless dosage transfer system, comprising in combination:

an ampule for storing a pharmaceutical product in a manner to inhibit lability of the product and permitting the transfer of the product in an aseptic manner to avoid nosocomial infection from ambient air comprising, in combination:

resilient walls that can be collapsed;

a sealable orifice adjacent said walls to pass a pharmaceutical grade solid therethrough;

and an opening on said ampule, said opening is circumscribed by a coupler which is to be complementally fastened to receive a dose administering device wherein said ampule further includes a cap for occluding said opening wherein said cap has a tab surface.

27. The system of claim 26 wherein said tab surface includes indicia thereon correlative of contents within the ampule.

* * * * *